(12) United States Patent
Yang et al.

(10) Patent No.: US 8,187,366 B2
(45) Date of Patent: May 29, 2012

(54) NATURAL GAS DESULFURIZATION

(76) Inventors: Ralph T. Yang, Ann Arbor, MI (US);
Yuhe Wang, Ann Arbor, MI (US); Luis Amestica, Santiago (CL)

(*) Notice: Subject to any disclaimer, the term of this patent is extended or adjusted under 35 U.S.C. 154(b) by 712 days.

(21) Appl. No.: 12/263,844

(22) Filed: Nov. 3, 2008

(65) Prior Publication Data
US 2009/0118528 A1    May 7, 2009

Related U.S. Application Data

(60) Provisional application No. 60/984,602, filed on Nov. 1, 2007.

(51) Int. Cl.
*B01D 53/48* (2006.01)
*C07F 1/08* (2006.01)

(52) U.S. Cl. ............ 95/135; 208/208 R; 423/244.01

(58) Field of Classification Search ............ 208/208 R; 423/230, 242.1, 244.01, 244.02; 95/135, 95/136, 148; 585/820
See application file for complete search history.

(56) References Cited

U.S. PATENT DOCUMENTS

| | | | |
|---|---|---|---|
| 3,416,293 A * | 12/1968 | Alexander | 95/136 |
| 4,455,286 A * | 6/1984 | Young et al. | 423/230 |
| 4,513,098 A | 4/1985 | Tsao | |
| 4,827,076 A | 5/1989 | Kokayeff et al. | |
| 4,830,733 A | 5/1989 | Nagji et al. | |
| 4,886,935 A | 12/1989 | Kokayeff et al. | |
| 5,190,908 A * | 3/1993 | Audeh et al. | 502/415 |
| 5,227,351 A * | 7/1993 | Gasper-Galvin et al. | 502/60 |
| 5,458,861 A | 10/1995 | Buchanan et al. | |
| 6,030,597 A | 2/2000 | Buchanan et al. | |
| 6,056,936 A | 5/2000 | Nougayrede et al. | |
| 6,251,348 B1 * | 6/2001 | Scranton, Jr. | 423/244.01 |
| 6,579,347 B1 * | 6/2003 | Wakita et al. | 95/135 |
| 6,610,264 B1 | 8/2003 | Buchanan et al. | |
| 6,875,410 B2 | 4/2005 | Satokawa et al. | |
| 7,029,574 B2 | 4/2006 | Yang et al. | |
| 7,053,256 B2 | 5/2006 | Yang et al. | |
| 7,063,732 B2 | 6/2006 | Katikaneni et al. | |
| 7,094,333 B2 | 8/2006 | Yang et al. | |
| 7,148,389 B2 | 12/2006 | Yang et al. | |
| 7,396,388 B2 * | 7/2008 | Mitariten | 95/123 |

(Continued)

FOREIGN PATENT DOCUMENTS
EP    1121977 A2 *    8/2001

(Continued)

OTHER PUBLICATIONS

European Search Report for European Application No. EP08846178 (Oct. 21, 2011).

(Continued)

*Primary Examiner* — Frank Lawrence, Jr.
(74) *Attorney, Agent, or Firm* — Nixon Peabody LLP

(57) ABSTRACT

A method for desulfurizing natural gas includes contacting the natural gas with an adsorbent which preferentially adsorbs at least one of hydrogen sulfide, COS, sulfur odorants, or combinations thereof, at a selected temperature and pressure, thereby producing desulfurized natural gas and an at least one of hydrogen sulfide/COS/sulfur odorant/combinations thereof-rich adsorbed component. The adsorbent includes a copper species adapted to form π-complexation bonds and direct metal-sulfur bonds with the at least one of hydrogen sulfide, COS, sulfur odorants, or combinations thereof, and wherein the preferential adsorption occurs by π-complexation and direct metal-sulfur bonding.

18 Claims, 9 Drawing Sheets

U.S. PATENT DOCUMENTS

| | | |
|---|---|---|
| 2002/0009404 A1 | 1/2002 | Tsybulevskiy et al. |
| 2004/0057890 A1 | 3/2004 | Satokawa et al. |
| 2004/0178117 A1 | 9/2004 | Morton et al. |
| 2006/0162557 A1 | 7/2006 | Kim et al. |

FOREIGN PATENT DOCUMENTS

| | | |
|---|---|---|
| WO | 2004/099351 A1 | 11/2004 |

OTHER PUBLICATIONS

Satokawa et al., "Adsorptive removal of dimethylsulfide and t-butylmercaptan from pipeline natural gas fuel on Ag zeolites under ambient conditions," Applied Catalysis B: Environmental 56: 51-56 (2005).

* cited by examiner

H$_2$S concentration (ppm)

NATURAL GAS DESULFURIZATION

This application claims the benefit of U.S. Provisional Patent Application Ser. No. 60/984,602, filed Nov. 1, 2007, which is hereby incorporated by reference in its entirety.

STATEMENT REGARDING FEDERALLY SPONSORED RESEARCH

This invention was made with government support under grant CTS-0455176 awarded by the National Science Foundation. The U.S. government has certain rights in the invention.

FIELD

The present disclosure relates generally to natural gas desulfurization.

BACKGROUND

Fuel cells, such as proton exchange membrane (PEM) fuel cells and solid oxide fuel cells (SOFC), are arguably the most energy efficient and clean energy generation systems. These fuel cells require hydrogen as the fuel. One method for producing hydrogen is by catalytic reforming of natural gas with liquefied petroleum gas (LPG), i.e., commercial propane and butane, used to a lesser extent. These fuels are often the fuels of choice for hydrogen because of their relative abundance and availability of supply infrastructure. Such fuels are often dosed with sulfur odorants, such as thiols and sulfides, for handling during transportation and utilization. Residual $H_2S$ may remain in these fuels (~5-10 ppm). It is desirable to remove these sulfur compounds before feeding to the catalytic reformers, in part, because they may poison both the catalysts in the reformers and the catalysts in the fuel cells.

The concentrations of sulfur in pipeline natural gas and LPG are typically around 10 ppm or higher. Raw natural gas from wellhead contains a significant amount of sulfur in the form of $H_2S$. The concentration varies widely from ppm levels up to 5%. The acceptable sulfur levels for reformers and fuel cells are well below 1 ppm, (for example, <0.01 ppm).

It is desirable that the $H_2S$ be removed to a level below 10 ppm before distribution in pipelines. Current technologies used to remove $H_2S$ include solvent extraction using amine solutions or adsorption at ambient temperatures using fixed bed adsorbers (e.g., activated carbon or zinc oxide (ZnO)). These sorbents generally do not have high sulfur selectivity and high sulfur capacity; and furthermore, they are used as disposable sorbents because they are not regenerable.

SUMMARY

A method for desulfurizing natural gas hydrocarbons includes contacting the natural gas with an adsorbent which preferentially adsorbs at least one of hydrogen sulfide, COS, sulfur odorants, or combinations thereof, at a selected temperature and pressure, thereby producing desulfurized natural gas and a hydrogen sulfide/COS/sulfur odorant/combinations thereof-rich adsorbed component. The adsorbent includes a copper species adapted to form π-complexation bonds and direct metal-sulfur bonds with the at least one of hydrogen sulfide, COS, sulfur odorants, or combinations thereof, and wherein the preferential adsorption occurs by π-complexation and direct bonding between metal and sulfur atoms.

An apparatus includes a reactor having a reactor chamber; at least one gas inlet to the reactor chamber; at least one gas outlet from the reactor chamber; at least one solid material inlet/outlet to the reactor chamber; and at least one adsorbent loaded in the reactor chamber, wherein the adsorbent includes a copper species adapted to form π-complexation and direct metal-sulfur bonds with the at least one of hydrogen sulfide, COS, sulfur odorants, or combinations thereof present in gas passing through the adsorbent.

BRIEF DESCRIPTION OF THE DRAWINGS

Features and advantages of embodiments of the present disclosure will become apparent by reference to the following detailed description and drawings.

DETAILED DESCRIPTION

Figure 1:
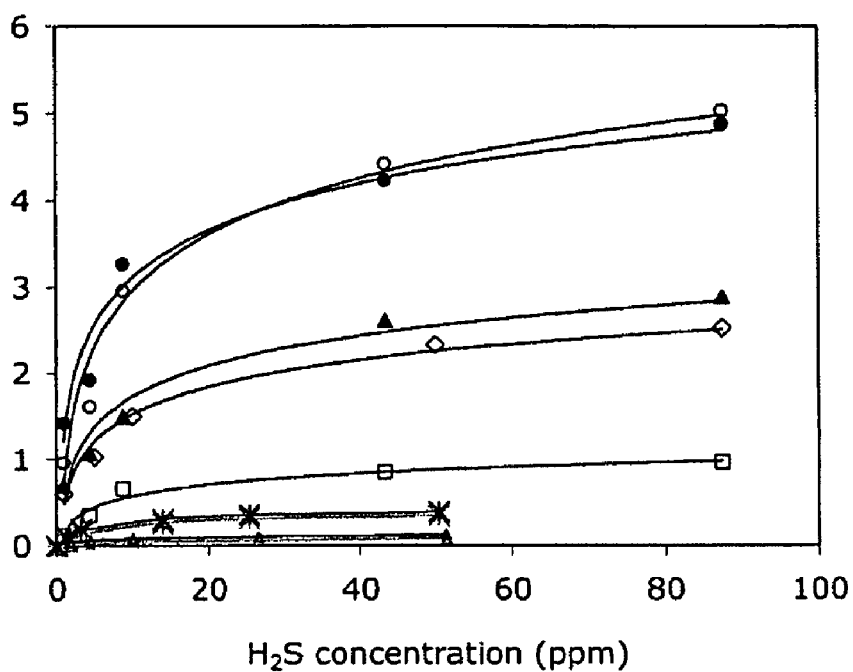
FIG. 1 is a graph depicting isotherms for $H_2S$ adsorption on different sorbents at 25° C., where Cu(I)Y (●); AgY (○); Cu(II)Y (▲); CuCl/SBA-15 (◇); Cu/AC (□); ACF (✖); SWNT (Δ); fitting data (line)

Embodiments of the method disclosed herein advantageously use sorbents that have high sulfur selectivity and capacity, ambient temperature operation and regenerability. The copper species of the sorbents used herein advantageously form strong bonds with $H_2S$, DOS, and sulfur odorant molecules (e.g., dimethyl sulfide), thereby rendering them useful for desulfurization of natural gas hydrocarbons.

The present inventive method may be used to remove sulfur compounds (for example, hydrogen sulfide and sulfur odorants) from natural gas hydrocarbons (including, but not limited to methane gas). Natural gas has a different composition than liquid fuels, and thus the copper species interacts differently with the compounds in the natural gas than it would with the compounds in liquid fuel. It is believed that preferential adsorption occurs via both π-complexation and direct bonding between metal and sulfur atoms.

Without being bound to any theory, it is believed that the higher sorbent capacity of the sorbents used herein may be due to a preferred sorbent pretreatment method wherein the sorbent is activated at a temperature ranging between about 250° C. and about 600° C., and is then cooled. In an embodiment, the activation may be carried out for an amount of time ranging between about one hour and about 20 or more hours. In an alternate embodiment, the activation may be carried out for an amount of time ranging between about 5 hours and about 15 hours. In a further embodiment, the activation may be carried out for an amount of time ranging between about 6 hours and about 12 hours. In an embodiment, the pretreatment process may take place in an inert and/or reducing atmosphere. As a non-limiting example, activation may take place in an inert atmosphere (e.g., helium) and/or in a reducing atmosphere, and cooling may take place in an inert atmosphere. Some non-limitative examples of the reducing atmosphere include reducing gases, such as, for example, hydrogen and/or carbon monoxide, and/or any other suitable reducing gas. As such, the pretreatment process results in a cuprous sorbent.

Further, the adsorbents used herein may be regenerated after use by any suitable method. In an embodiment, the regenerating may be accomplished by calcining the adsorbent. The calcining may be carried out for any suitable length of time and at any suitable temperature sufficient to substantially remove the $H_2S$/COS/sulfur odorants from the adsorbent. In an embodiment, the calcining may be carried out for an amount of time ranging from about less than 1 hour to about 20 or more hours. In an alternate embodiment, the calcining may be carried out for an amount of time ranging between about 5 hours and about 15 hours. In an embodiment, the calcining may be carried out at a temperature ranging between about 300° C. and about 600° C. As a non-limiting example, desulfurization may be accomplished for sorbents calcined between about 6 hours and about 12 hours at a temperature ranging between about 350° C. and 450° C. The sorbents used in the methods disclosed herein, one example of which is Cu(I)Y, may be substantially fully regenerated by first calcining/air (and/or oxygen) oxidation (e.g., at about 350° C.), followed by auto-reduction in an inert atmosphere (e.g., at about 450° C.).

The method disclosed herein may advantageously be run at ambient temperature and pressure, which is highly desirable for a variety of reasons. In one embodiment, the natural gas is pipeline natural gas. It is much less energy consuming to run processes at ambient temperature and pressure. Further, conventional catalytic desulfurizing processes are typically run at high temperatures, e.g., 700° C., and high pressures, causing the (very expensive) catalyst to be continually deactivated. Still further, the method disclosed herein may be used as a first line desulfurizing process, and/or as a clean up desulfurizing process to remove sulfur compounds missed by conventional processes. It may be very useful to have the option to use the method disclosed herein as a downstream "clean up" desulfurizing process, in that it may not be necessary to revamp current refining processes upstream from the present inventive process. This option could solve the cost-prohibitive problems encountered by some refiners. In another embodiment, the natural gas is present in ambient air. The adsorbent can be loaded into portable containers for removing sulfur-containing compounds from various environments, such as mine chambers and other work areas where workers may be exposed to sulfur-containing gases. In one embodiment, the adsorbent can be loaded into a canister for a gas-mask.

Higher sorbent capacity may also be due to a natural gas pretreatment process. Such processes may be accomplished in order to remove, for example, hydrocarbons from the gas. The natural gas may be pretreated using a desiccant or a non-sulfur selective sorbent that removes hydrocarbons that are heavier than methane. Non-limiting examples of suitable desiccants include activated alumina, silica gel, activated carbon and/or combinations thereof. Non-limiting examples of suitable non-sulfur selective sorbents include activated carbon, silica gel, zeolites (e.g., 3A-zeolite), activated alumina and/or combinations thereof.

In some embodiments, a relatively thin layer of another sorbent may be used as a guard bed to remove moisture. It is contemplated that all suitable commercial sorbents, particularly 3A-zeolite and desiccants, may be used as a guard bed. In one non-limiting embodiment, a guard bed may be included as about 25% of the bed at the inlet thereto; while the main bed is a copper ion-exchanged zeolite.

Although the process disclosed herein has specifically tested Cu—Y (among others), it is to be understood that Type X zeolites may in some cases be as good as, or better zeolites than Y zeolites, since more cations are available in X zeolites. Further, it is to be understood that other zeolites are contemplated as being within the scope of the present disclosure. Still further, the adsorbent disclosed herein may include a mesoporous support (e.g., MCM-41, SBA-15, and the like).

The copper species form π-complexation and direct metal-sulfur bonds with $H_2S$, COS, sulfur odorants, and/or combinations thereof. Non-limiting examples of such copper species include $Cu^{2+}$ and $Cu^+$ salts. Further, the copper species does not need to be ion-exchanged, but rather may be dispersed (monolayer dispersion, island dispersion, etc.) on a carrier (such as, for example, silica, alumina, etc.) by any suitable method know in the art.

The π-complexation bonds and direct metal-sulfur bonds are stronger than those formed by van der Waals interactions, but they are also weak enough as to be broken by traditional engineering means such as increasing temperature and/or decreasing pressure. Therefore, the present inventors have fortuitously tailored and developed methods where selective adsorption is needed, such as in the case of sulfur removal from natural gas hydrocarbons.

In an embodiment, the process for desulfurizing natural gas includes contacting the natural gas with an adsorbent which preferentially adsorbs hydrogen sulfide, COS, sulfur odorants, and/or combinations thereof at a selected temperature and pressure. This process produces desulfurized natural gas and a hydrogen sulfide, COS, sulfur odorants and/or combinations thereof adsorbed component. It is to be understood that in the "hydrogen sulfide, COS, sulfur odorants and/or combinations thereof adsorbed component" term as used herein, the sulfur compounds may not represent the greatest amount of adsorbate.

The adsorbent includes any ion-exchanged zeolite or mesoporous support, including high surface area supports, but in a non-limiting example, the zeolite/support is selected from zeolite X, zeolite Y, zeolite LSX, MCM-41, SBA-15, silicoaluminophosphates (SAPOs), and mixtures thereof. Generally, the zeolite has exchangeable cationic sites, and at least some of the sites have the copper species present. The mesoporous support is reacted with copper salts to form a monolayer of the support and salt.

The adsorbent includes sulfur containing compounds, including but not limited to compounds of general formula:

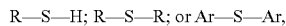

R—S—H; R—S—R; or Ar—S—Ar, where R represents an aliphatic ligand and Ar represents an aromatic ligand, wherein the ligand is capable of not interfering with the formation of p-complexation by steric hinderance.

Figure 16:
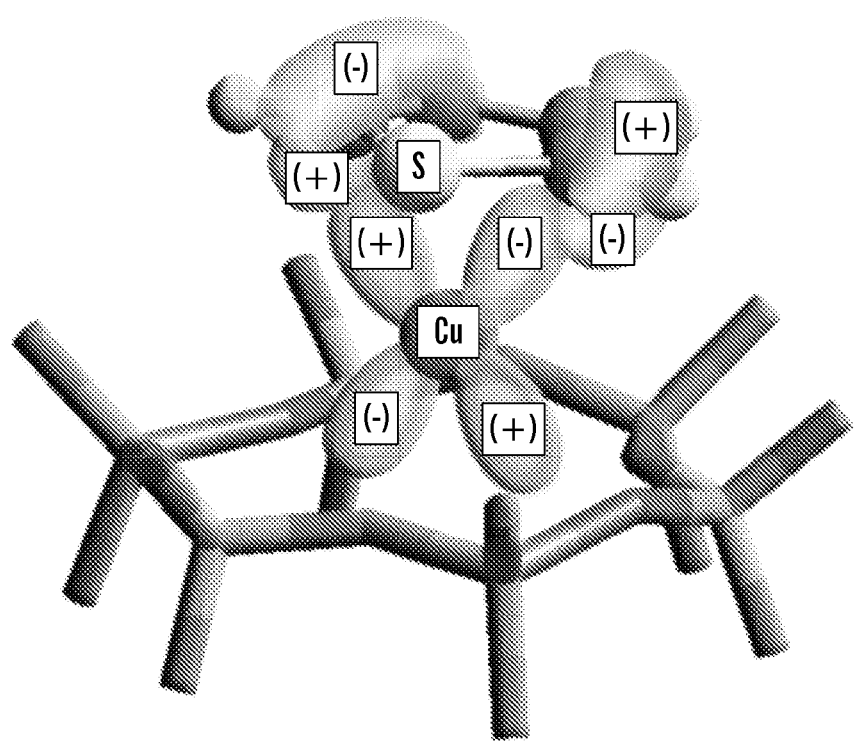
FIG. 16 is a molecular orbital image of an intermediate complex formed by a method in accordance with the present invention.

An intermediate complex of general formula:

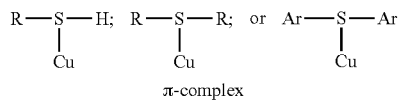

π-complex where R represents an aliphatic ligand and Ar represents an aromatic ligand, wherein the ligand is capable of not interfering with the formation of p-complexation by steric hinderance, is formed where Cu is π-bonded to the sulfur containing compound of the complex as depicted in the molecular orbital image shown in FIG. 16.

As previously mentioned, the preferential adsorption occurs by π-complexation and direct metal-sulfur bonding. Generally, the copper species releasably retains hydrogen sulfide, COS, sulfur odorants and/or combinations thereof when present.

To further illustrate the present disclosure, the following examples are given. It is to be understood that these examples are provided for illustrative purposes and are not to be construed as limiting the scope of the present disclosure.

EXAMPLES

Sorbent Preparation

The starting adsorbent materials were Na—Y zeolite (Si/Al=2.40 and 2.43, Strem Chemicals), and NH$_4$—Y zeolite (Si/Al=2.40, Strem Chemicals). H—Y zeolite was obtained after calcination of NH$_4$—Y with dry air at 450° C. at 1° C./min. All of the zeolites were modified by either liquid phase or vapor phase exchange techniques.

To form the vapor phase exchanged zeolites, layers of the proton-form zeolite and CuCl (99.99%, Sigma-Aldrich) were loaded into a reactor each separated by thin quartz wool walls. Direct contact of the zeolite and salt is not desirable, in part because of disproportionation of the copper species in the presence of adsorbed water. The reactor was then heated in an inert, dry atmosphere, from room temperature to about 200° C. at 1° C./min. The temperature was held at that point for about 4 to 6 hours. The temperature was then slowly increased above the normal melting point of CuCl (430° C.) and maintained at a pre-specified high temperature for another 10 hours. The CuCl excess was completely evaporated from within the voids of the zeolite. This was corroborated by the absence of the salt from its original reactor location at the end of the vapor phase ion exchange (VPIE) process and by a white crystalline ring formed at the reactor outlet. The zeolite was then treated in oxygen at 200° C. for about 4 to 6 hours before cooling down to room temperature.

AgY (Comparative Example) was prepared by two consecutive ion exchanges with 0.05 M solution of AgNO$_3$. Each exchange was carried with twice the required amount of cations for theoretical full exchange at room temperature with agitation for 24 hours. The solution was decanted after the first exchange, and then a fresh AgNO$_3$ solution was added and the mixture was agitated again at room temperature for 24 hours. After the second exchange, the mixture was vacuum filtered and washed in copious amount of deionized water until no free ions were present in the filtrate (i.e., no precipitation upon treatment with NaCl). The AgY was dried at room temperature and atmospheric conditions in a dark area.

It is to be understood, that Cu(I)Y may be prepared in the same fashion as that noted above for the preparation of AgY. That is, Cu(I)Y may be prepared by liquid phase ion exchange with Cu(NO$_3$)$_2$ followed by calcination and treatment in a reductive atmosphere.

CuCl/MCM-41 and CuCl/SBA-15 samples were prepared by spontaneous monolayer dispersion. The MCM-41 and SBA15 were prepared, and then activated in a dry He atmosphere at 550° C. for two hours. After this, about 1.0 g of MCM-41 or SBA-15 was thoroughly mixed with 1.32 g or 0.97 g of CuCl and the mixture was placed in a quartz tube and heat treated at 380° C. in He for 24 hours. After this heat treatment, a monolayer CuCl/MCM-41 or CuCl/SBA-15 sample was obtained. The BET surface areas, N$_2$ adsorption isotherms and pore size distribution of the samples were measured by physical adsorption of N$_2$ at 77 K using a Micromeritics ASAP 2020. The pore sizes of MCM-41 and SBA-15 based adsorbents were calculated by BJH methods. The results are listed Table 1 (below).

TABLE 1

Physical properties of mesoporous absorbents

| Adsorbent | Metal loading (mmol/g) | BET surface area (m2/g) | BJH pore diameter (Å)$^a$ | BJH pore volume (cm3/g)$^b$ |
|---|---|---|---|---|
| MCM-41 | — | 1225 | 28.7 | 1.17 |
| CuCl/MCM-41 | 5.7 | 456 | 26.0 | 0.33 |
| SBA-15 | — | 901 | 58.7 | 1.14 |
| CuCl/SBA-15 | 5.1 | 411 | 54.2 | 0.56 |

$^a$BJH desorption average pore diameter (4 V/A).
$^b$BJH desorption cumulative volume of pores between 17.0 Å and 3000.0 Å diameter.

Adsorption of Dimethyl Sulfide (DMS) and Hydrogen Sulfide (H$_2$S)

Single component isotherms for DMS and H$_2$S were measured using standard gravimetric method at room temperature (25° C.) and 60° C. A Shimadzu TGA-50 automatic recording microbalance was employed. Helium (UHP. 99.999%) was used as the carrier gas and was first passed through a 3A zeolite to remove trace amount of water. The mixtures of DMS/He and H$_2$S/He were also pretreated using a 3A-zeolite. The desired H$_2$S/DMS concentration was reached by diluting with additional He (the total flow rate was 200 ml/min), and the mixture was directed into the microbalance. Calibrations for gas composition changes were made to accurately account for differences in buoyancy and friction loss.

Cu(I)Y (VPIE) zeolites were obtained by auto-reduction of Cu(II)Y(VPIE) using the ultra-high purity helium gas pretreated by 3A-zeolite and after heating to 450° C. at 1° C./min. The temperature was held at the set point for about 10 hours. The temperature was then brought to room condition under inert gas flow followed by TGA experiment. Cu(II)Y (VPIE) was pretreated in air at 350° C. for 6 hours followed by TGA experiment. Cu/AC (Sud-chemie) was obtained by pretreating in He at 350° C. for 6 hours followed by TGA experiment. BPL carbon was pretreated in He for 5 hours in He at 250° C. followed by TGA experiment. AgY (LPIE) was pretreated in air at 350° C. for 6 hours followed by TGA experiment.

Ab Initio Molecular Orbital Calculations

Molecular orbital (MO) studies on the π-complexation bonding for $H_2S$ and DMS on Cu(I), Ag and Cu(II) zeolites were performed. The Gaussian 03 package and Cerius2 molecular modeling software were used for all MO calculations. Geometry optimizations and frequency analysis were performed at the Hartree-Fock (HF) level first, then binding energy analysis was performed at density functional theory (DFT) level using effective core potentials (ECPs).

Models for Cu-Zeolites: Cu(I)Z & Cu(II)Z and Ag-Zeolite: Ag Z

As used throughout the examples, Cu(I)Z, Cu(II)Z and AgZ represent zeolites or Y zeolites. The zeolite model has the molecular formula of $H_{12}Si_3Al_3O_{18}$. Since the framework of zeolites is composed of silica and alumina groups, represented by $SiO_4$ and $AlO_4$ respectively, the model zeolite consisted of three $SiO_4$ and three $AlO_4$ joined together in an alternate manner through shared oxygen atoms to form a six-membered oxygen ring. Such a six-membered ring cluster is truncated from a faujasite zeolite model in Cerius2. The oxygen dangling bonds are saturated with hydrogen in order to terminate the model. A cation $Cu^+$ or $Cu^{2+}$ or $Ag^+$ is placed in the center of the ring; the exact position is determined by optimization with zeolite atoms fixed to their crystallographic positions. This model represents cations located on site II (SII) sites in faujasite, the most likely exposed site. Once the optimized structures of zeolite models are obtained at the HF/LanL2DZ level, then an adsorbate molecule such as $H_2S$ is added onto the cation of zeolite model, the resulting structure is further optimized, and the energy of the optimized structure is determined at the B3LYP/LanL2DZ level.

Geometry Optimization and Bond Energy Calculations

Frequency analysis was used to verify that all geometry optimized structures were true minima on the potential energy surface. The optimized structures were then used for bond energy calculations according to the following expression:

$$E_{ads} = E_{adsorbate} + E_{adsorbent} - E_{adsorbent-adsorbate} \quad (1)$$

where $E_{adsorbate}$ is energy of free adsorbate, $E_{adsorbent}$ is energy of free adsorbent and $E_{adsorbent-adsorbate}$ is energy of the adsorbate/adsorbent system. A higher value of $E_{ads}$ corresponds to a stronger adsorption.

Characterization of Sorbents

Previous analysis indicates that Ag/Al and Na/Al ratios in AgY were 1.13 and 0.01, respectively. This is because $Ag^+$ is known to have higher selectivity to cation sites in zeolites compared to $Na^+$. More than 100% Ag ion exchange ratios were obtained in AgY, because some Ag was located outside the charge-compensating sites. For Cu(I)Y prepared by VPIE, almost complete ion exchange was reached. The composition of the different sorbents is shown in Table 2.

TABLE 2

Composition of different sorbents

| Adsorbent | Composition | Preparation |
|---|---|---|
| Cu(I)Y | Cu54H3Al57Si135O384 | VPIE at 700° C. and autoreduction at 450° C. |
| Cu(II)Y | (CuOH)54H3Al57Si135O384 | VPIE at 700° C. and pretreat at 350° C. |
| AgY | Ag63Al57Si135O384 | LPIE and pretreat at 350° C. |
| Cu/AC | 5%(wt)Cu/Active Carbon | from Süd-Chemie |

$H_2S$/DMS Adsorption Isotherms at 25° C.

FIG. 1 shows the equilibrium isotherms of $H_2S$ on different sorbents at 25° C. The solid lines in the figure also show the data fitted by the Langmuir-Freundlich isotherm, because Langmuir isotherm alone would not adequately fit the data, Crespo et al., "Superior Sorbent for Natural Gas Desulfurization," *Ind. Eng. Chem. Res.* 47:1238-1244 (2008); Hernandez-Maldonado et al., "Desulfurization of Diesel Fuels by Adsorption via π-Complexation with Vapor-Phase Exchanged Cu(I)—Y Zeolites," *J. Am. Chem. Soc.* 126:992-993 (2004); Ma et al., "Selective Adsorption of Sulfur Compounds: Isotherms, Heats, and Relationship between Adsorption from Vapor and Liquid Solution," *Ind. Eng. Chem. Res.* 46:2760-2768 (2007); Li et al., "Effects of Oxygenates and Moisture on Adsorptive Desulfurization of Liquid Fuels with Cu(I)Y Zeolite," *Catalysis Today* 116:512-518 (2006); Yang et al., "Desulfurization of Transportation Fuels with Zeolites Under Ambient Conditions," *Science* 301:79-81 (2003), which are hereby incorporated by reference in their entirety. The hybrid Langmuir-Freundlich isotherm is given by:

$$q = \frac{q_m B P^{1/n}}{1 + B P^{1/n}} \quad (2)$$

All of the sorbents have very high capacities for $H_2S$, even at the very low concentration level (0.5 ppm). The capacity of the adsorption decreased in the order of Cu(I)Y>AgY>Cu(II)Y>Cu/AC. The $H_2S$ adsorption capacity on the Cu(I)Y and AgY is very similar. These results indicate that both Cu(I)Y and AgY are excellent sorbents for $H_2S$ adsorption removal (while the cost of Ag is much higher than that of Cu).

Figure 2:
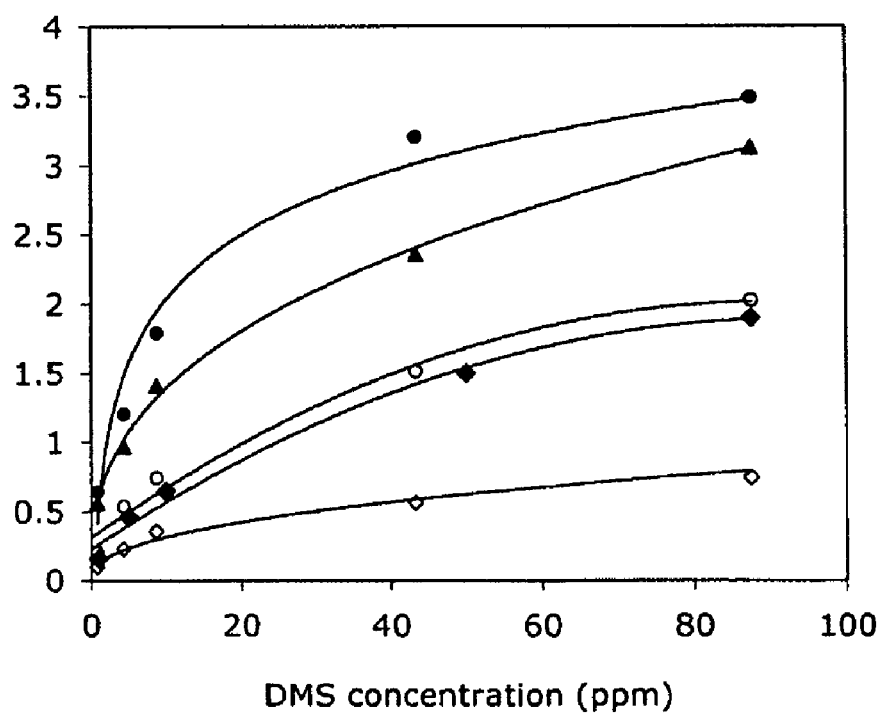
FIG. 2 is a graph depicting isotherms for DMS adsorption on different sorbents at 25° C., where Cu(I)Y (●); AgY (▲); Cu(II)Y (○); CuCl/SBA-15 (◆); Cu/AC (◇); fitting data (line)

FIG. 2 shows the equilibrium isotherms of DMS on different sorbents at 25° C. The data was fitted by the Langmuir-Freundlich isotherm, also shown by the solid lines in the figure. It can be seen that all sorbents have very high capacities for DMS, even at the very low concentration level (0.5 ppm). The capacity of the adsorption decreased in the order of Cu(I)Y>AgY>Cu(II)Y>Cu/AC in the whole DMS concentration range.

From FIGS. 1 and 2, it is clearly shown that the adsorption capacity of $H_2S$ is higher than that of DMS for each sorbent, which was predicted from the molecular orbital calculations that showed stronger bonds with $H_2S$ than DMS. The parameters for the measured adsorption isotherms of $H_2S$ and DMS are summarized in Table 3.

TABLE 3

Langmuir-Freundlich parameters for adsorption of $H_2S$ and DMS at 25° C.

| Adsorbent | Adsorbate | qm (mmol/g) | B (ppm-(1/n)) | n |
|---|---|---|---|---|
| AgY | $H_2S$ | 6.35 | 0.16 | 1.40 |
|  | DMS | 39.21 | 0.015 | 2.59 |
| Cu(I)Y | $H_2S$ | 7.15 | 0.24 | 2.03 |
|  | DMS | 4.70 | 0.14 | 1.44 |
| Cu(II)Y | $H_2S$ | 5.08 | 0.14 | 1.97 |

TABLE 3-continued

Langmuir-Freundlich parameters for adsorption of H$_2$S and DMS at 25° C.

| Adsorbent | Adsorbate | qm (mmol/g) | B (ppm-(1/n)) | n |
|---|---|---|---|---|
| | DMS | 6.50 | 0.04 | 1.83 |
| Cu/AC | H$_2$S | 0.97 | 0.11 | 0.81 |
| | DMS | 1.59 | 0.084 | 1.93 |

The temperature dependence of the Langmuir-Freundlich isotherm parameters (q$_m$, B and n) can be estimated from Table 3. The theoretical temperature dependence of the Langmuir constant, B, is approximately (by neglecting the effect of T in the pre-exponential factor):

$$B \propto e^{E/RT} \quad (3)$$

where E is the heat of adsorption (in positive value).

The temperature dependence of q$_m$ can be estimated using the empirical "Gurvitsch Rule," i.e., q$_m$ is equal to the pore volume divided by the molar volume of the adsorbate (as liquid). Thus, the temperature dependence of q$_m$ follows that of the liquid density. Since n is an empirical parameter, there is no theoretical basis for the temperature dependence of n. A linear correlation between n and T would be a good approximation.

H$_2$S/DMS Adsorption Isotherms at 60° C.

Figure 3:
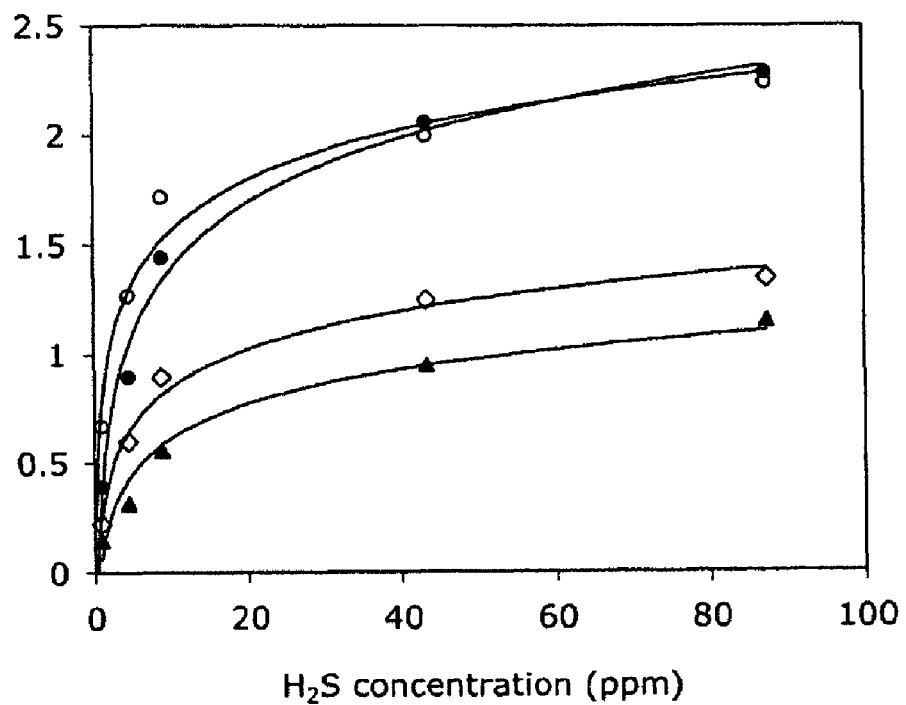
FIG. 3 is a graph depicting isotherms for $H_2S$ adsorption on different sorbents at 60° C., where Cu(I)Y (○); AgY (●); Cu(II)Y (◇); Cu/AC (▲); fitting data (line)
Figure 4:
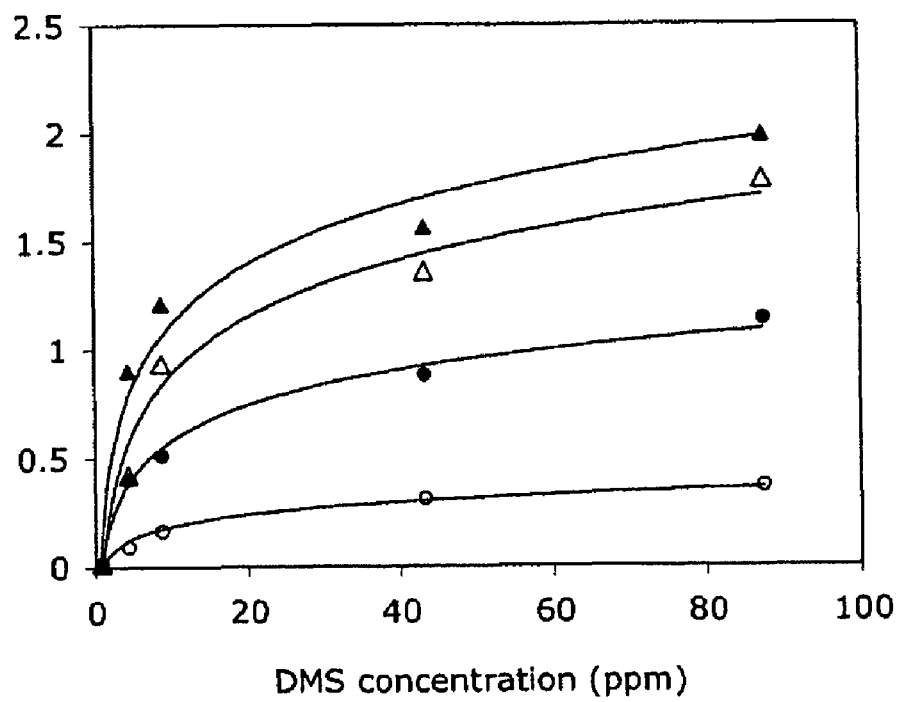
FIG. 4 is a graph depicting isotherms for DMS adsorption on different sorbents at 60° C., where CuY (▲); AgY (Δ); Cu(II)Y (●); Cu/AC (○); fitting data (line)

FIG. 3 shows the isotherm of H$_2$S on different sorbents at 60° C. The data were also fitted by the Langmuir-Freundlich isotherm shown as the solid lines in the figure. A similar trend was observed on these isotherms, when compared to the isotherms at 25° C. The adsorption capacity decreases in the following order: Cu(I)Y>AgY>Cu(II)Y>Cu/AC. FIG. 4 shows the isotherm of DMS on different sorbents at 60° C. The data fitted by Langmuir-Freundlich isotherm were also shown as the solid lines in FIG. 4. The results were also very similar to those at 25° C. The parameters for the measured adsorption isotherms of H$_2$S and DMS are summarized in Table 4.

TABLE 4

| Adsorbent | Adsorbate | qm (mmol/g) | B (ppm-(1/n)) | n |
|---|---|---|---|---|
| CuY | H$_2$S | 2.36 | 0.43 | 1.33 |
| | DMS | 1.85 | 0.11 | 0.73 |
| Cu(II)Y | H$_2$S | 1.44 | 0.19 | 1.05 |
| | DMS | 1.38 | 0.10 | 1.21 |
| AgY | H$_2$S | 2.32 | 0.13 | 0.87 |
| | DMS | 1.78 | 0.06 | 0.83 |
| Cu/AC | H$_2$S | 1.61 | 0.10 | 1.40 |
| | DMS | 0.42 | 0.06 | 0.96 |

CH$_4$ Adsorption Isotherms

Figure 5:
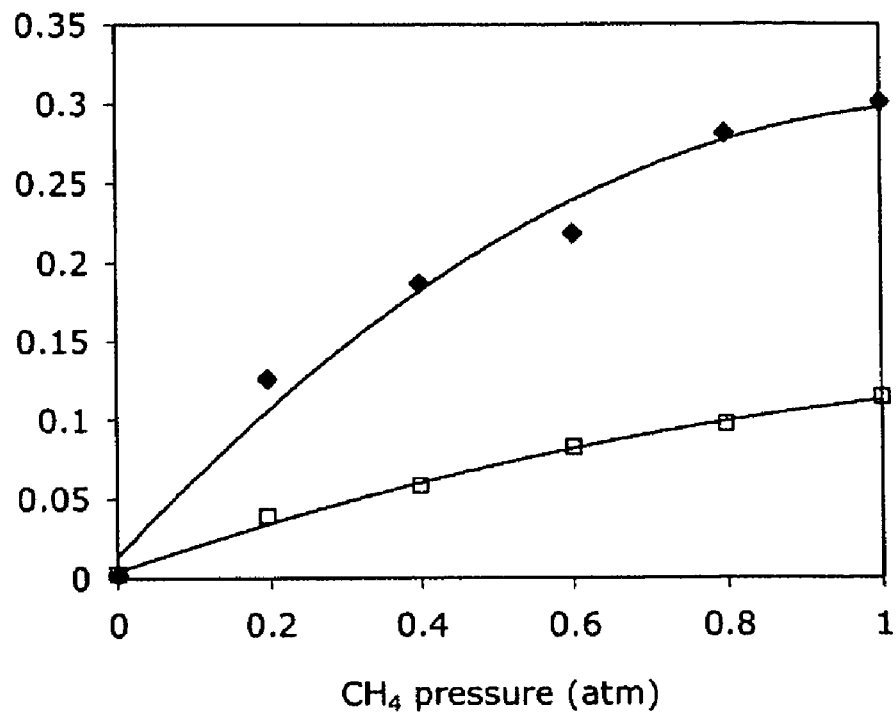
FIG. 5 is a graph depicting isotherms of $CH_4$ on Cu(I)Y at different temperatures, 25° C. (◆); 60° C. (□)

Methane isotherms were measured, in part because it is the major component of natural gas. The adsorption isotherms of CH$_4$ on Cu(I)Y and AgY were measured at room temperature (25° C.) and 60° C. It was found (see FIG. 5) that a very small amount of CH$_4$ was adsorbed compared to the sulfur compounds, even at much higher pressures, which means these sorbents have high selectivity on sulfur compounds and still maintain a high sulfur capacity.

Adsorption Energies

Adsorption energies were calculated from experimental data for the different sulfur species (H$_2$S and DMS) on the different sorbents. Adsorption isotherm data was used along with the Clausius-Clapeyron equation to obtain the heats of adsorption. The Clausius-Clapeyron equation is given by:

$$\frac{d(\ln P)}{d\left(\frac{1}{T}\right)} = \frac{\Delta H}{R}$$

The obtained results are summarized in Table 5 (below). As can be seen from the results, the adsorption energies follow the order Cu(I)Y>AgY>Cu(II)Y for both H$_2$S and DMS.

TABLE 5

Energies of adsorption in kcal/mol for sulfur adsorbates (obtained from experimental isotherm data)

| Adsorbate | ΔE on Cu(I)Y | ΔE on AgY | ΔE on Cu(II)Y |
|---|---|---|---|
| H$_2$S | −14.0 | −11.4 | −9.5 |
| DMS | −11.3 | −7.9 | −6.6 |

Moreover, the heats of adsorption for H$_2$S are higher than that of DMS for all adsorbents. This is in fair agreement with the results from the molecular orbital calculations, shown in Table 6.

TABLE 6

Energies of adsorption in kcal/mol for sulfur adsorbates (from ab initio molecular orbital calculations)

| Adsorbate | ΔE on Cu(I)Z | ΔE on AgZ | ΔE on Cu(II)Z |
|---|---|---|---|
| H$_2$S | −17.5 | −16.1 | nil |
| DMS | −13.2 | −7.8 | −1.3 |

Regeneration of Cu(I)Y by Heating in Inert Gas

The regeneration of the spent Cu(I)Y was investigated by heating in inert gas at different temperatures. Table 7 shows the desorption amounts of H$_2$S and DMS on Cu(I)Y at different heating temperatures. When the sorbent was heated at 200° C., the amounts desorbed were 1.01 and 1.47 mmol/g for DMS and H$_2$S, respectively, which corresponded to 59% and 45% of the original amount for the fresh sample. When the used sample was treated at 450° C., 87% of DMS and 69% H$_2$S were desorbed. Based on these results, it can be concluded that, on the Cu(I)Y sorbent, the adsorption energy of H$_2$S is higher than that of DMS, so the adsorbed DMS was relatively easily removed. This is in agreement with the adsorption energy results. CuY could be regenerated completely (100% regeneration) by reacting with air at 350° C. followed by auto-reduction.

TABLE 7

Desorption amount of DMS and H$_2$S on Cu(I)Y

| Regeneration Conditions | DMS (mmol/g) | H$_2$S (mmol/g) |
|---|---|---|
| Fresh | 1.7 | 3.23 |
| Heat at 200° C. in He gas | 1.01 | 1.47 |
| Heat at 300° C. in He gas | 1.30 | 1.76 |
| Heat at 450° C. in He gas | 1.48 | 2.23 |

Breakthrough Experiments

Figure 6:
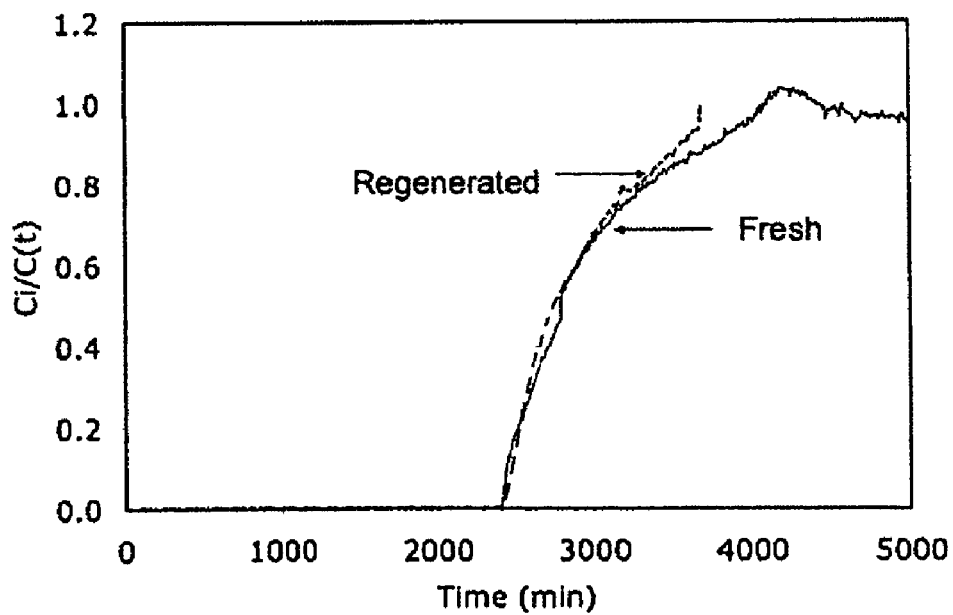
FIG. 6 is a graph depicting breakthrough of DMS on fresh and regenerated Cu(I)-Y diluted in 3A zeolite 20/50 wt/wt with GHSV=27,000 $h^{-1}$ at 50° C.

Fixed-Bed breakthrough experiments were carried out to investigate the adsorption capacity of the different sorbents and compare their effectiveness in removing sulfur compounds at different flow conditions. DMS diluted in He was used as the sulfur containing compound since it is the most difficult odorant to remove from the studied compounds. High adsorption capacity samples were diluted with 3A zeolite to provide a longer fixed-bed and allow the use of less amount of adsorbent sample in order to make the experiment length more manageable. DMS is not adsorbed in 3A due to pore size exclusion, so it is an excellent choice as a diluent. Furthermore, the experiments were carried out at an elevated temperature (50° C.) to decrease the amount of time per run since the samples have a lower capacity at higher temperature. The sample (typically 70-100 mg) was then placed on a vertical glass adsorber (6 mm ID) with a quartz frit. The reactor was wrapped with a heating tape and insulated with ceramic wool wrapping. A thermocouple was placed at the reactor surface to monitor the temperature. The temperature was controlled with a PID temperature controller. The outlet of the reactor was connected to a GC-FID to continually monitor the gas as it exited the column. The breakthrough of DMS on VPIE Cu(I)Y is shown in FIG. 6. The run was repeated after regenerating the sample in air at 350° C. for 8 hours followed by auto-reduction. As can be seen, the adsorption capacity is almost identical to the fresh capacity, which further proves the sorbent is fully regenerable.

Figure 7:
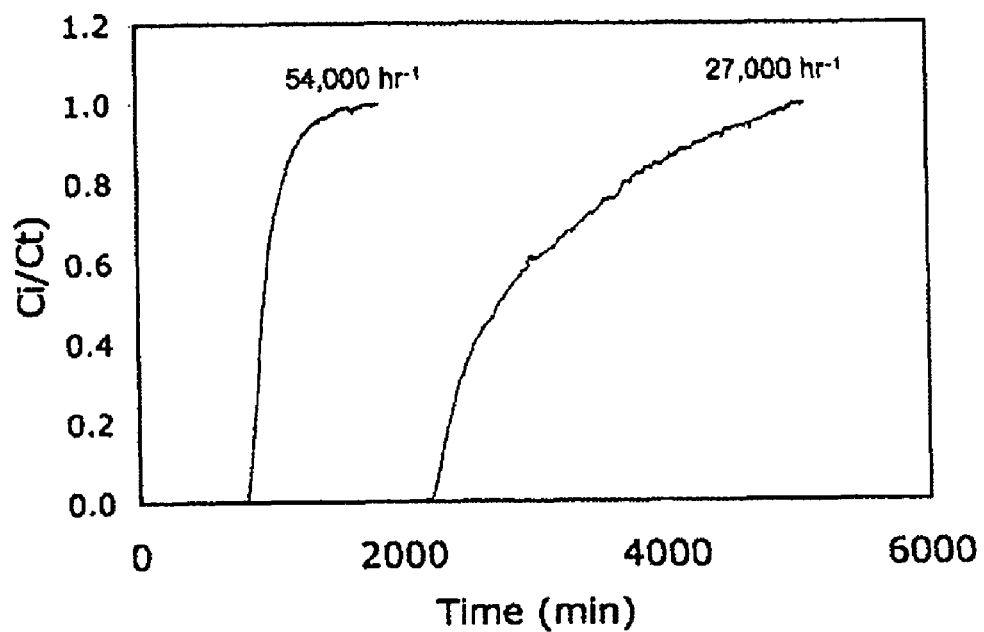
FIG. 7 is a graph depicting breakthrough of DMS 10 ppmw on Cu(I)-Y diluted in 3A zeolite 20/50 wt/wt at different GHSV and 50° C.

The effect of different gas flowrates (Gas Hourly Space Velocity, GHSV) is shown in FIG. 7. As expected, under the same conditions, a higher flowrate led to a lower adsorption capacity.

Figure 8:
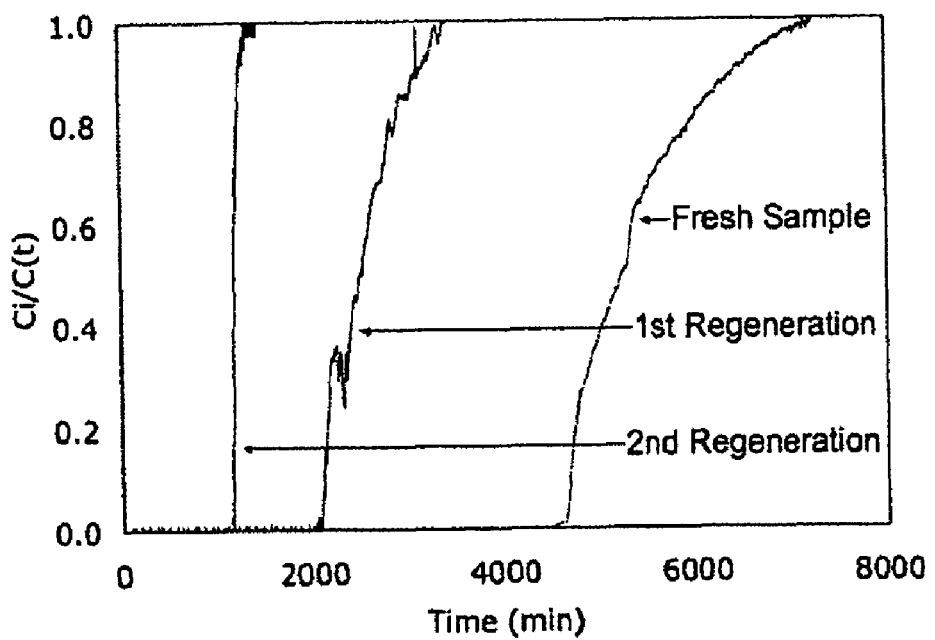
FIG. 8 is a graph depicting breakthrough of DMS 10 ppmw on AgY diluted in 3A zeolite 20/50 wt/wt at GHSV=27 000 and 50° C.
Figure 9:
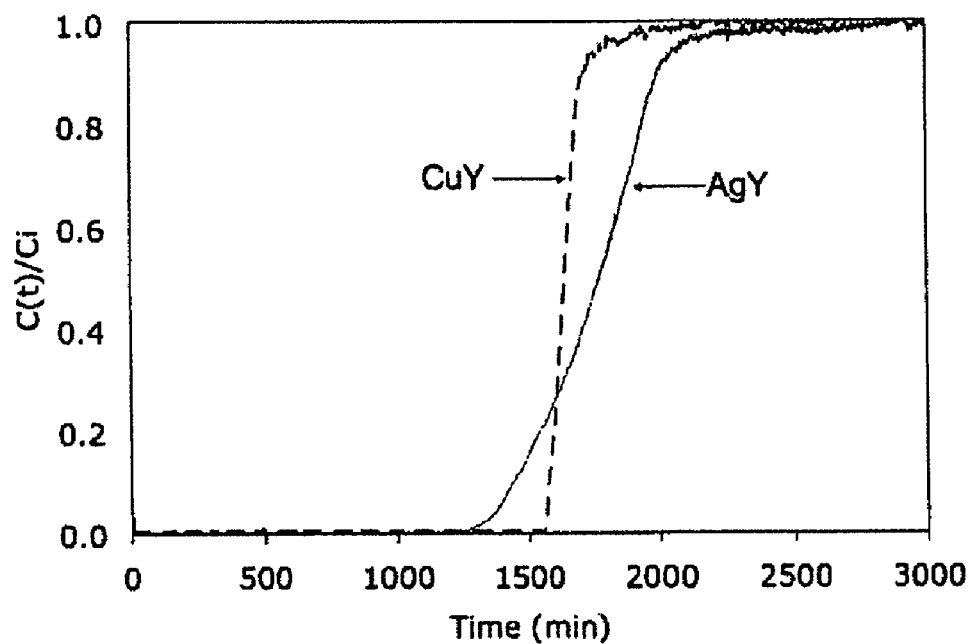
FIG. 9 is a graph depicting breakthrough of DMS 98.4 ppmw on Cu(I)-Y and Ag—Y at GHSV=39,000 $hr^{-1}$ and 25° C.

To compare the copper species sorbents with AgY zeolite, the effect of regeneration were investigated for DMS on Ag—Y zeolite. The results are shown in FIG. 8. As can be seen, the capacity is roughly halved after each regeneration cycle. The effect of different flowrates was not investigated due to the severe adsorption capacity reduction after regenerating. A direct comparison between fresh samples of VPIE Cu(I)-Y and Ag—Y can be seen in FIG. 9. The breakthrough capacity is higher for VPIE Cu(I)-Y, however, the total adsorption capacity is slightly higher for Ag—Y. This agrees with the isotherm data at higher concentrations where AgY has a higher capacity than Cu(I)Y.

Figure 10:
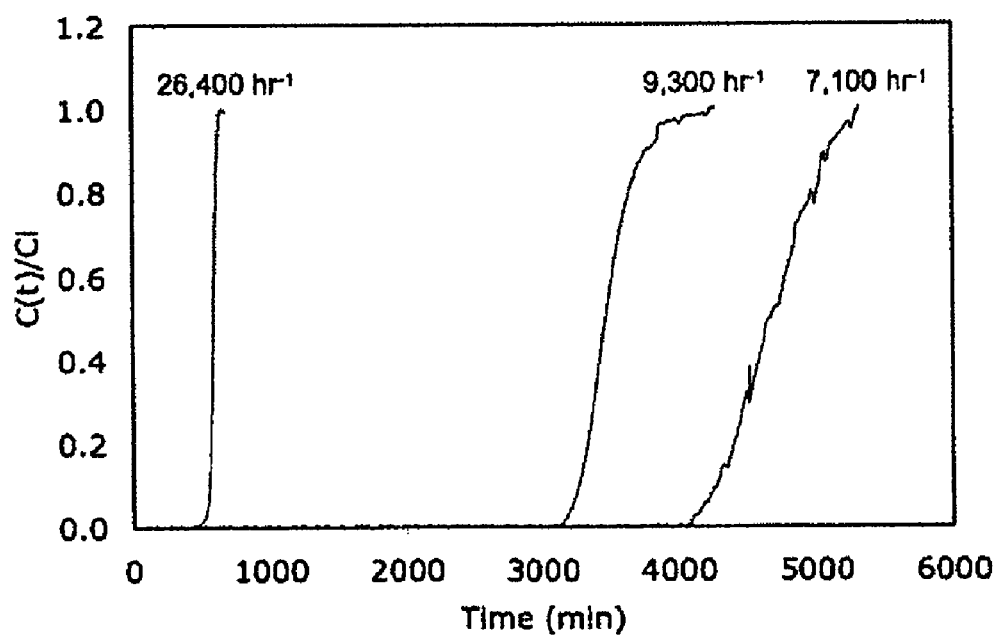
FIG. 10 is a graph depicting breakthrough for DMS 92.8 ppmw on active carbon at 50° C. and different GHSV.
Figure 11:
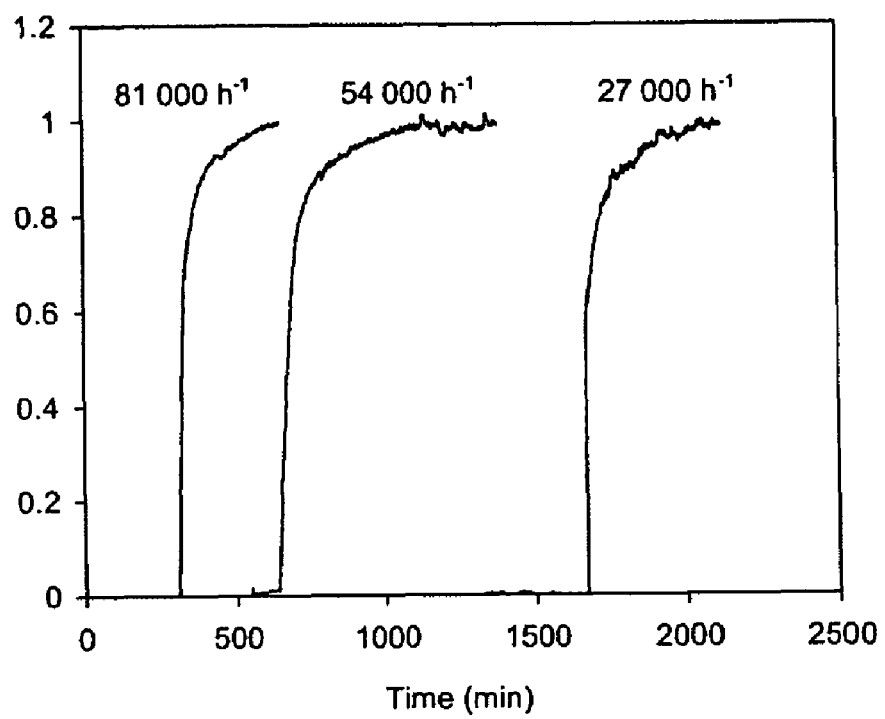
FIG. 11 is a graph depicting breakthrough of DMS on CuCl/SBA-15 at different GHSV and 25° C.
Figure 12:
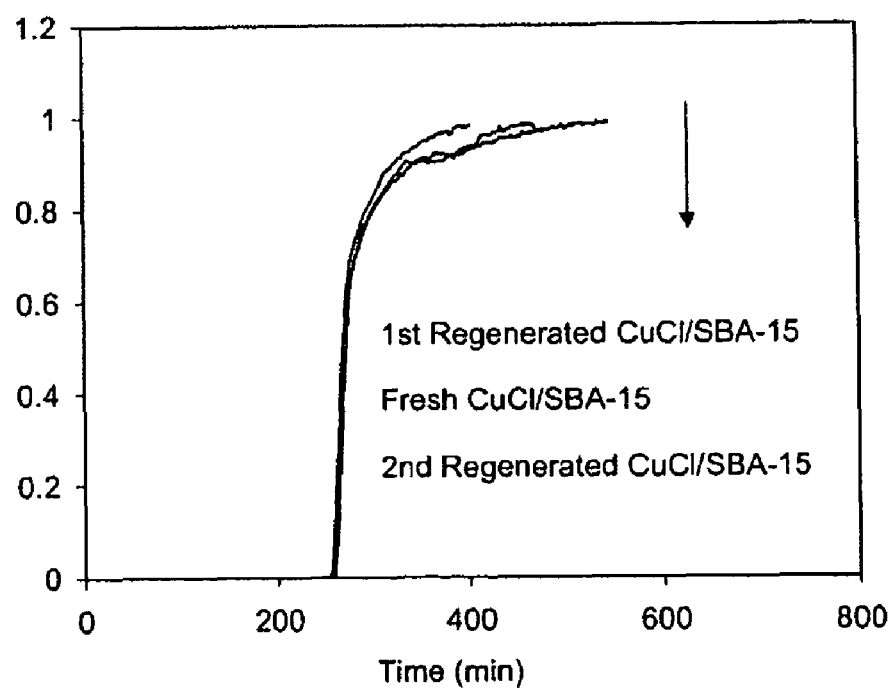
FIG. 12 is a graph depicting breakthrough of DMS on fresh and regenerated CuCl/SBA-15 with GHSV=60 000 $h^{-1}$ at 25° C.
Figure 13:
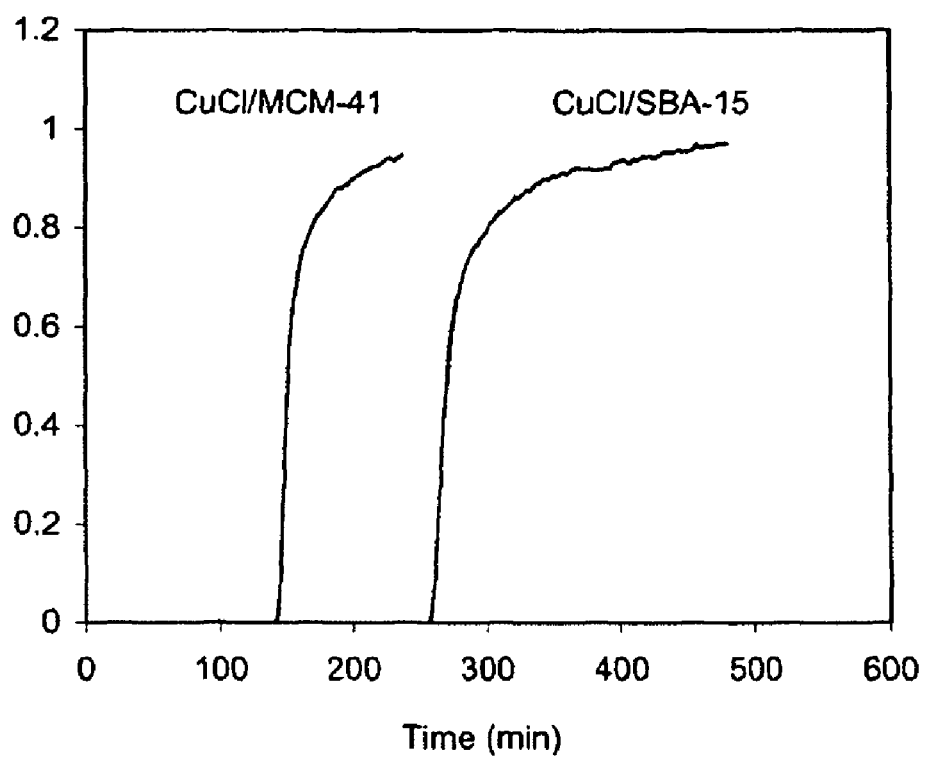
FIG. 13 is a graph depicting breakthrough of DMS on fresh CuCl/MCM-41 and CuCl/SBA-15 with GHSV=60 000 $h^{-1}$ at 25° C.

The mesoporous sorbents (based on MCM-41 and SBA-15) were studied next. These sorbents have very large and uniform pore sizes, as shown in Table 1 (above). FIGS. 10 and 11 show the flowrate effect on the adsorption of DMS on activated carbon and CuCl/SBA-15. Again, the adsorption capacity decreases with increasing flowrate. Given the relatively high adsorption capacity of CuCl/SBA-15, second and third adsorption cycles were performed to verify the capacity of the regenerated material (see FIG. 12). As can be seen, the sample is also fully regenerable. FIG. 13 shows the comparison of two different materials with large pore sizes: CuCl/MCM-41 and CuCl/SBA-15. It is clear that CuCl/SBA-15 outperforms CuCl/MCM-41 in the breakthrough capacity (at the same space velocity), due, at least in part, to the much larger pores of CuCl/SBA-15.

In all examples, the breakthrough occurs well before the equilibrium amount is reached. This can be attributed to slow rate of pore diffusion. There are two main factors affecting these results. First, the gas flowrate used in the experiments is rather high and thus, there is not enough time to reach equilibrium and early breakthrough occurs. The time required to achieve full adsorption capacity using such low flowrates is believed to be well over 300 days, and thus is not practical. Second, it was observed that the samples with smaller pores (zeolites) adsorb a lower fraction of the equilibrium amount than the larger pore samples (CuCl/SBA-15 and Active Carbon). It is possible that adsorbed molecules or some of the redox products (RS—Cu) may accumulate at the pore entrance and partially hinder the diffusion of other gas molecules, effectively reducing the rate of diffusion. This would explain the shape of the obtained breakthrough curves, which are very sharp, as opposed to the expected breakthrough, which should be slant and slowly increase to the inlet concentration. A similar case can be made for AgY zeolite. This phenomenon does not seem so dramatic in larger pore samples. The fact that both small and large pore samples are affected by this reduced capacity leads to diffusion limitation.

Second Adsorption Cycle Isotherms

Figure 14:
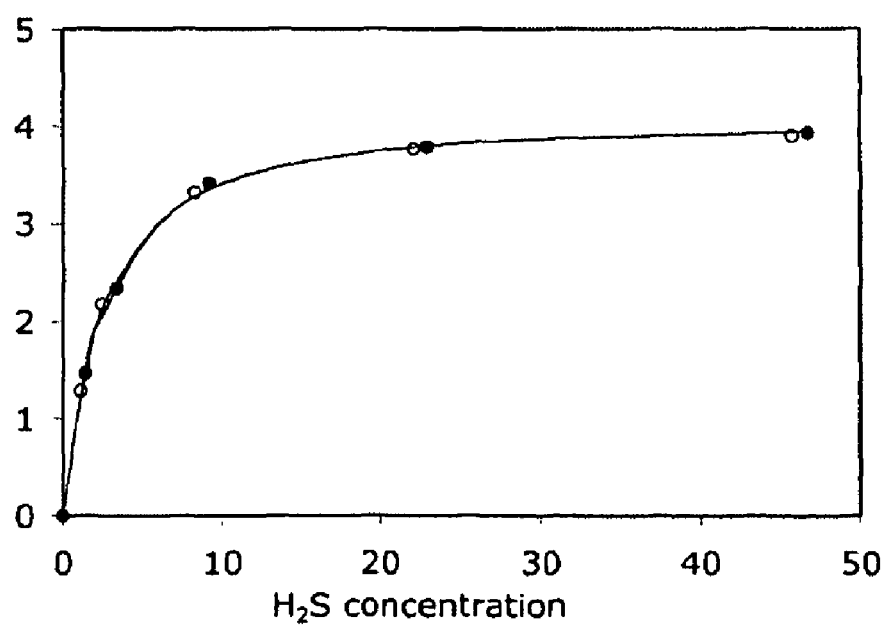
FIG. 14 is a graph depicting isotherms for $H_2S$ adsorption on VPIE Cu(I)-Y at 25° C., where fresh Cu(I)-Y (●); regenerated Cu(I)-Y (○); fitting data (line)
Figure 15:
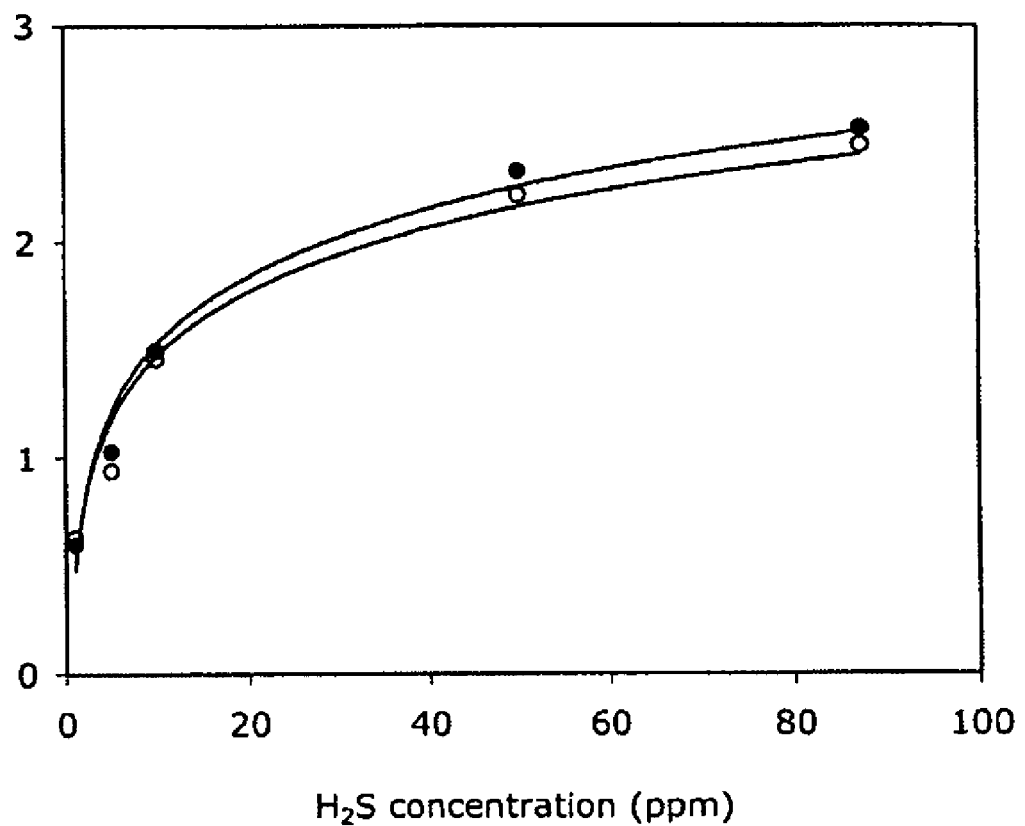
FIG. 15 is a graph depicting isotherms for $H_2S$ adsorption on CuCl/SBA-15 at 25° C., where fresh CuCl/SBA-15 (●); regenerated CuCl/SBA-15 (○); fitting data (line)

Second adsorption cycle isotherms were measured for the materials that showed both relatively high adsorption capacity from the fresh sample adsorption isotherms and full regeneration in the breakthrough experiments, namely VPIE Cu(I)-Y and CuCl/SBA-15. FIGS. 14 and 15 show these isotherms and the results confirm the breakthrough experiments results, both samples are fully regenerable. In this case, VPIE Cu(I)-Y was regenerated in air at 350° C. for 8 hours, and CuCl/SBA-15 was regenerated in He at 350° C.

In the examples herein, the sulfur adsorption capacity was measured for various sorbent materials. It was found from ab initio molecular orbital calculations that the energy of adsorption of $H_2S$ was greater than that of DMS on both Cu(I)Y and AgY; furthermore, the energy of adsorption decreased in the following order Cu(I)Y>AgY>Cu(II)Y. Energies of adsorption calculated by molecular orbital theory and that by Clausius-Clapeyron equation using experimental data showed good agreement and the same trends. Breakthrough curves show early breakthrough (i.e., below equilibrium), likely due to diffusion limitation. Lower flowrates increased the breakthrough capacity. Cu(I)Y and AgY show the highest adsorption capacities from among the tested samples. However, when regeneration capacity was tested, Cu(I)Y displays superior performance by being fully regenerable. Furthermore, the Cu(I)Y shows little affinity for CH4 which is desirable for natural gas desulfurization. CuCl supported on mesoporous supports (MCM-41 and SBA-15) are also superior sorbents because they are also fully regenerable and have the largest pore sizes, allowing less diffusion resistance. Thus, the results show that Cu(I)Y, CuCl/SBA-15 and CuCl/MCM-41 are the most preferred sorbents for natural gas desulfurization.

It will be understood by anyone skilled in the art that the object of the present invention may be carried out in a variety of reactor types. In one example, a reactor may contain at least one gas inlet, appropriate controls for handling gas flow as typically known to those of skill in the art, at least one gas outlet, and at least one solid material inlet/outlet for loading adsorbent, for example, zeolite materials. In addition, the reactor apparatus preferably includes at least one controller, as typically known to those of skill in the art, for controlling the pressure and temperature of the reactor chamber from about room temperature to about 700° Celcius. The preferred operating temperature, pressure and flow rate is typically dependent upon various factors including reactor geometry and known to those of skill in the art. Preferably, the reactor is loaded with a guard bed formed by layered beds of adsorbent materials. In a further embodiment, two or more such reactors are operated in tandem, one being used for desulfurization of gas while another is being used for regeneration of the adsorbent material.

While several embodiments have been described in detail, it will be apparent to those skilled in the art that the disclosed embodiments may be modified. Therefore, the foregoing description is to be considered exemplary rather than limiting.

What is claimed is:

1. A method for desulfurizing natural gas hydrocarbons, the method comprising:
    contacting the natural gas with an adsorbent which preferentially adsorbs at least one of hydrogen sulfide, COS, sulfur odorants, or combinations thereof, at a selected temperature and pressure, thereby producing desulfurized natural gas and a hydrogen sulfide, COS, sulfur odorant, or combinations thereof-rich adsorbed component, wherein the adsorbent comprises a $Cu^+$ species adapted to form π-complexation and direct metal-sulfur bonds with the at least one of hydrogen sulfide, COS, sulfur odorants, or combinations thereof, and wherein the preferential adsorption occurs by π-complexation and direct metal-sulfur bonding.

2. The method of claim 1, wherein the natural gas is pipeline natural gas, and wherein the sorbent adsorbs hydrogen sulfide and sulfur odorants.

3. The method of claim 2, wherein the sulfur odorants are dimethyl sulfide.

4. The method of claim 1, wherein the adsorbent is activated by pretreatment at a temperature ranging between about 250° C. and about 600° C. and for a time ranging between about one hour and about 20 hours, followed by cooling.

5. The method of claim 4, wherein the adsorbent is activated in a reductive atmosphere.

6. The method of claim 1, further comprising pretreating the natural gas using a desiccant.

7. The method of claim 6, wherein the desiccant is selected from activated alumina, silica gel, activated carbon and combinations thereof.

8. The method of claim 1, further comprising pretreating the natural gas using a non-sulfur selective sorbent that removes hydrocarbons heavier than methane.

9. The method of claim 1, wherein the adsorbent further includes a zeolite or a mesoporous support.

10. The method of claim 1, wherein prior to contacting the natural gas with the adsorbent, the method further comprises pretreating the adsorbent, the pretreatment process comprising the steps of:
activating the adsorbent at a temperature ranging from about 250° C. to about 600° C. in an inert or reducing atmosphere for an amount of time ranging between about one hour and about 20 hours; and
then cooling the adsorbent in an inert atmosphere.

11. The method of claim 1, wherein the selected temperature is ambient temperature and the selected pressure is ambient pressure.

12. The method of claim 1, wherein the adsorbed component comprises compounds of the formula:

R—S—H; R—S—R; or Ar—S—Ar, wherein R represents an aliphatic ligand and Ar represents an aromatic ligand, and wherein the ligands are capable of not interfering with the formation of p-complexation by steric hinderance.

13. An intermediate complex of the formula:

R—S(Cu)—H; R—S(Cu)—R; or Ar—S(Cu)—Ar, produced by the process of claim 1, wherein R represents an aliphatic ligand and Ar represents an aromatic ligand, wherein the ligands are capable of not interfering with the formation of p-complexation by steric hinderance, and wherein $Cu^+$ is π-bonded to the sulfur containing compound.

14. The method of claim 1, further comprising regenerating the adsorbent by calcining the adsorbent.

15. The method of claim 1, wherein the adsorbent comprises Cu(I)Y or supported Cu+ compounds on high area surface substrates.

16. The method of claim 1, wherein the adsorbent comprises an ion-exchanged zeolite or mesoporous support.

17. The method of claim 1, wherein the natural gas is present in ambient air.

18. The method of claim 1, wherein the adsorbed component comprises compounds of the formula:

R—S(Cu)—H; R—S(Cu)—R; or Ar—S(Cu)—Ar, wherein R represents an aliphatic ligand and Ar represents an aromatic ligand, wherein the ligands are capable of not interfering with the formation of p-complexation by steric hinderance, and wherein $Cu^+$ is π-bonded to the sulfur containing compound.

\* \* \* \* \*